United States Patent [19]

Otterlei et al.

[11] Patent Number: 5,169,840
[45] Date of Patent: Dec. 8, 1992

[54] DIEQUATORIALLY BOUND BETA-1, 4 POLYURONATES AND USE OF SAME FOR CYTOKINE STIMULATION

[75] Inventors: Marit Otterlei; Terje Espevik; Gudmund Skjak-Brock; Olav Smidsrod, all of Trondheim, Norway

[73] Assignees: Nobipols Forskningsstiftelse, Trondheim; Protan Biopolymer A/S, Drammen, both of Norway

[21] Appl. No.: 676,103

[22] Filed: Mar. 27, 1991

[51] Int. Cl.$^5$ .................... A61K 30/12; C12R 1/91; C12R 5/00; C12R 5/02

[52] U.S. Cl. .................... 514/55; 514/8; 514/929; 514/54; 514/908; 536/2; 536/3; 536/20; 536/127; 536/114; 536/123; 435/89.1; 424/85.2

[58] Field of Search .................... 514/55, 8, 929, 54, 514/908; 536/127, 114, 123, 2, 3, 20; 435/69.1; 424/85.2

[56] References Cited

U.S. PATENT DOCUMENTS

| | | | |
|---|---|---|---|
| 4,578,458 | 3/1986 | Pier | 536/123 |
| 4,605,623 | 8/1986 | Malette et al. | 514/55 |
| 4,840,941 | 6/1989 | Ueno et al. | 514/55 |
| 4,963,354 | 10/1990 | Shepard et al. | 514/21 |
| 4,965,271 | 10/1990 | Mandell et al. | 514/929 |
| 5,002,759 | 3/1991 | Gaffar et al. | 514/54 |

OTHER PUBLICATIONS

Painter et al.; Carbohydrates Research, 140 (1985) 61-68; "New Gluco-noglucans Obtained by Oxidation of Amylose at Position 6".

Skjak-Braek et al.; Carbohydrate Research, 154 (1986) 239-250; "Monomer Sequence & Acetylation Pattern In Some Bacterial Alignates".

Browning et al.; Journal of Immunology; 138(9), 2857-63; "Interferon Blocks Interleukin 1-induced Prostaglandin Release From Human Peripheral Monocytes".

Holter et al.; Journal of Immunology; 138(9), 2917(22); "Expression of Functional IL-2 Receptors by Lipolysaccharides and Interferron-γStdm Human Monocytes".

*Primary Examiner*—Ronald W. Griffin
*Attorney, Agent, or Firm*—Blakely, Sokoloff, Taylor & Zafman

[57] ABSTRACT

The present invention is directed to a material and method for the stimulation of the production of cytokines. Several polysaccharides, including polymers of different size of ⊕1-4 linked D-mannuronic acid (poly-M and M-blocks), chitosan and cellulose oxidized in C-6 position C60XY) induce human monocytes to produce the cytokines. Preferably, the molecular weights of poly-M and chitosan are above 50,000 and 20,000 respectively. Pretreatment of the monocytes with IFN-γ increases the cytokine production from monocytes stimulated with all polysaccharides tested. The subject polysaccharides worked in vivo and in vitro.

The present invention has therapeutic utility as vaccine adjuvants and components. Therapeutic compositions comprising biologically active quantities of the compositions of the present invention may be employed to potentiate antibody production in response to vaccine antigens. Anti-tumor, anti-bacteriological, anti-fungal and anti-viral effects may be expected.

16 Claims, 5 Drawing Sheets

Poly-M

D-ManA $(^4C_1)$ $\xrightarrow{\beta(1-4)}$ D-ManA $(^4C_1)$ $\xrightarrow{\beta(1-4)}$ D-ManA $(^4C_1)$ $\xrightarrow{\beta(1-4)}$ D-ManA $(^1C_4)$

M-BLOCKS

D-ManA $(^4C_1)$ $\xrightarrow{\beta(1-4)}$ D-ManA $(^4C_1)$ $\xrightarrow{\beta(1-4)}$ L-GulA $(^1C_4)$ $\xrightarrow{\alpha(1-4)}$ D-ManA $(^4C_1)$

C6OXY

D-GlcA $(^4C_1)$ $\xrightarrow{\beta(1-4)}$ D-GlcA $(^4C_1)$ $\xrightarrow{\beta(1-4)}$ D-GlcA $(^4C_1)$ $\xrightarrow{\beta(1-4)}$ D-GlcA $(^4C_1)$

CHITOSAN

D-GlcNAc $(^4C_1)$ $\xrightarrow{\beta(1-4)}$ D-GlcN $(^4C_1)$ $\xrightarrow{\beta(1-4)}$ L-GlcNAc $(^4C_1)$ $\xrightarrow{\beta(1-4)}$ D-GlcN $(^4C_1)$

G-BLOCKS

L-GulA $(^1C_4)$ $\xrightarrow{\alpha(1-4)}$ L-GulA $(^1C_4)$ $\xrightarrow{\alpha(1-4)}$ L-GulA $(^1C_4)$ $\xrightarrow{\alpha(1-4)}$ L-GulA

DIEQUATORIALLY BOUND BETA-1, 4 POLYURONATES AND USE OF SAME FOR CYTOKINE STIMULATION

BACKGROUND OF THE INVENTION

1. Field of the Invention

This invention relates to the fields of biochemistry and immunology. More specifically, this invention provides a method of in vivo and in vitro stimulation of the production of cytokines for various medicinal, biochemical and physiological effects.

2. Art Background

The lymphocytes or white blood cells in the animal body come in two types, B-cells and T-cells. The B-cells produce antibodies in the form of immunoglobulins that bind onto invading organisms while the T-cells produce the lymphokines or cytokines which are responsible for turning B-cells on or off. It is well known that the growth of normal lymphocytes is dependent not only on contact with an antigenic substance or a mitogen, but also on the presence of certain factors known as lymphokines or cytokines.

The known types of lymphokines include IL-2, B-cell factors, macrophage activation factor (MAF), Interleukin-3 (IL-3), Colony Stimulating Factor (CSF), Tumor Necrosis Factor (TNF), and other factors produced by monocytes such as Interleukin-1 (IL-1) and Gamma Interferon. All of these factors are secreted by white blood cells and are collectively known as cytokines.

Monocytes can be stimulated by various agents, such as LPS (lipopolysaccharides), to produce certain cytokines including TNF, IL-1 and IL-6. LPS contain a polysaccharide and a lipid A part. Polysaccharides such as $\beta$1-3 glucans and blocks of $\beta$1-4 D-mannuronic acid have been reported to stimulate monocytes to produce cytokines. Seljelid R., Figenschau Y., Bogwald J., Rasmussen L. T. and R. Austgulen. 1989. Evidence that Tumour Necrosis Induced by Aminated $\beta$1-3D Polyglucose is Mediated by a Concerted Action of Local and Systemic Cytokines. Scand. J. Immunol., 30:687; Otterlei M., Ostgaard K., Skjåk-Br k G., Smidsrod O. and T. Espevik. 1991. Induction of cytokine production from human monocytes stimulated with alginate, J. of Immunotherapy, in press.

The present invention relates generally to cytokines, and particularly to the stimulation of biologically active mammalian IL-1, IL-6 and TNF. Interleukin-1 is the designation given to a family of polypeptides, released by macrophages and certain other cell types in response to immunogenic and traumatic stimulation, which have a primary role in initiating host response to injury and infection. These cytokines have been associated with a complex spectrum of biological activities. Specifically, IL-1 is a primary immunostimulatory signal capable of inducing thymocyte proliferation via induction of Interleukin-2 release, and of stimulating proliferation and maturation of B lymphocytes. In addition, IL-1 has been linked with prostaglandin production, induction of fever and promotion of wound healing.

In recent years, immunotherapy has become more and more important in the field of applied medicine. For instance opportunistic infections are frequently observed in newborn children with functional immunodeficiency, cancer patients, patients transplanted with bone marrows, patients receiving chemotherapeutic agents or steroids, and aged patients. Antibiotics so far used in these field against infections do not exert significant effect in immuno-deficient or immuno-depressed patients. The situation is almost the same in viral infections, and effective chemotherapeutic agents against viral infections has not been so far provided for clinical uses. Interferon has been reported to have some effects against viral infections; however, the nature of the interferons is still unclear and there is uncertainty as to the action modes. Therefore, interferon has not yet been confirmed for its effectiveness. The uncertainty of the effectiveness of interferon is also due to the fact that human interferon does not function in animal model. The presents of species-specificity may be one of the major difficulty for the development of interferon as therapeutic agents.

In the field of cancer, the situation of the development of effective therapeutic drugs is analogous to those in infectious diseases and viral diseases. In cancer patients, the prominent depression of immunological function of the host has been widely confirmed, and therefore immunotherapy and immunochemotherapy (adjuvant therapy) have drawn much attention as new definite methods to treat cancer patients. Immunotherapy has been said not only to restore or potentiate the specific immune responses against cancer, but also to improve the general function of host including immunological functions. So far several immunomodulators have been applied in clinics, however almost all of these share the nature of chemotherapeutic agents in such a manner that they also exert direct cytocidal effects against neoplastic cells.

Recently, an immunotherapeutic agent identified as an antitumor polysaccharide was confirmed for its clinical effectiveness in phase III clinical test. This agent exerts its antitumor effects by augmenting the reactivity of pre-effector cells to several kinds of cytokines.

Generally speaking, several antigens or immunogens containing the antigens are also used as vaccines in active immunotherapy. However the active immunotherapy does not function when the immunological functions of the host are depressed or defective such as in cancer, infections and viral diseases. In order to augment humoral immune responses, the administration of gamma-globulin together with the vaccines might be useful. However, when cell-mediated immunity play key roles, the methods is not practical. In such cases, cytokines might be useful when used in combination with vaccines such as tumor specific antigens instead of gamma-globulin in the augmentation of humoral immune responses.

Additionally, research has demonstrated that IL-1, TNF, and other leukocyte derived cytokines are important, and even critical, mediators in a wide variety of inflammatory states and diseases. The immunostimulating activities of cytokines may be important for treatment of neoplastic as well as for infectious diseases, and may have potential anti-tumor, anti-bacteriological anti-fungal and antiviral effects. Additionally, therapeutic compositions comprising biologically active quantities of certain cytokines and derivatives could be employed to potentiate antibody production in response to vaccine antigens. Also, in view of potential therapeutic utility as vaccine adjuvants and components of wound-healing compositions, there is interest in employing cytokines in veterinary medicine.

SUMMARY OF THE INVENTION

The present invention is directed to materials and methods for the stimulation of the production of cytokines. It has been found herein that several well-defined polysaccharides, including polymers of different size of β1-4 linked D-mannuronic acid (poly-M) and cellulose oxidized in C-6 position (C6OXY), and chitosan induces human monocytes to produce TNF-α. Poly-M was the most potent polysaccharide tested, approximately equal to LPS from *E. coli* which is already known as a cytokine stimulator.

TNF-α production was shown to depend strongly on the molecular weight of poly-M and chitosan, with a maximal TNF-α production for a m.w. above 50,000 and 20,000 respectively.

Pretreatment of the monocytes with IFN-γ increases the TNF-α production from monocytes stimulated with all polysaccharide tested in a similar way as for monocytes stimulated with LPS. C6OXY injected intravenously in mice led to rapid production of TNFα and IL-6. While not being bound to any particular theory on the mode of action, the results suggest that β1-4 linked polysaccharides and LPS may stimulate monocytes by similar mechanisms.

In view of potential therapeutic utility as vaccine adjuvants and components of wound-healing compositions, the present invention may be employed as such an agent. Therapeutic compositions comprising biologically active quantities of the compositions of the present invention may be employed to potentiate antibody production in response to vaccine antigens. Anti-tumor, anti-fungal, anti-bacteriological and anti-viral effects may be expected.

The present invention relates to several polysaccharides that are capable of stimulating cytokine producing cells to produce significant quantities of cytokines both in vivo and in vitro. This discovery makes possible a novel therapeutic approach in the treatment of bacterial, fungal and viral infections, cancer, immune deficiencies and autoimmune diseases.

Accordingly, it is an object of the invention to provide several compositions that are useful as therapeutic agents.

It is also an object of the invention to provide a novel method for producing in vitro cytokines, such as lymphokines and induce receptors to these cytokines.

It is also an object of the invention to produce in vivo cytokines for the treatment of various diseases such as cancer, immune deficiencies, autoimmune diseases and infectious bacterial and viral diseases.

It is also an object of the invention to provide novel pharmaceutical compositions that are based on the invented compositions and methods that produce cytokines in vivo and in vitro.

DETAILED DESCRIPTION OF THE INVENTION

As used herein, the terms and expressions "leukocyte derived cytokines," lymphokines and cytokines are to be given a broad meaning. Specifically, the term "leukocyte" as used herein means mammalian cells of granulocytic and lymphocytic lineage. Examples of leukocyte cells are polymorphonuclear leukocytes, such as neutrophils, and mononuclear phagocytes, such as monocytes and macrophages and lymphocytes.

The terms "cytokine" and "lymphokines" as used herein mean a secretory product of a leukocyte, and in particular a non-antibody protein released by a leukocyte on contact with antigen and which acts as an intercellular mediator of immune response. Examples of cytokines that are within the scope of this invention are chemotactic factors, factors promoting replication of lymphocytes, factors inhibiting replication of lymphocytes, factors affecting macrophage adherence, factors affecting enzyme secretion by macrophages, and factors that mediate secretion of oxidizing agents, such as oxygen, superoxide, hydrogen peroxide and hydroxyl radical. Specifically, TNF, IL-1 and IL-6 have been tested as being representative of the various cytokines which may be found.

MATERIALS AND METHODS

Polysaccharides

The monomer composition and sequential arrangement as well as the degree of polymerization ($DP_n$) of the different polysaccharides used in the present invention were analyzed by ¹H-n.m.r. spectroscopy on a Bruker 400 WM spectrometer as described previously by Grasdalen et al. ("A p.m.r. studie of composition and sequence of uronate residues in alginate"; Carbohydr Res 1979; 68:23); see also, Grasdalen H. 1983. High-field ¹H-n.m.r. spectroscopy of alginate: sequencial structure and linkage conformation. Carbohydr. Res., 118:255).

M-blocks consisting of more than 95% D-mannuronic acid (D-ManA) were isolated from the intracellular substance of *Ascophyllum nodosum* fruiting bodies as described by Haug et al. ("Correlation between chemical structure and physical properties of alginates" *Acta chem scand* 1967:21:768). The M-blocks had a $DP_n = 30-35$.

G-blocks consisting of more than 90% L-guluronic acid (L-GulA) and with a $DP_n = 25-30$ were isolated from the algea *Laminaria diqitata* by the method described by Haug et al. ("Studies on the sequence of uronic acid residues in alginic acid 1967:21:691).

A high molecular weight homopolymeric β1-4 linked D-ManA (poly-M) was isolated from liquid cultures of *Pseudomonas aeruginosa* DE 127 grown at low temperatures as described previously (Skjåk-Br k G., Grasdalen H. and B. Larsen. 1986. Monomer sequence and acetylation pattern in some bacterial alginates. Carbohyd. Res., 154:239). The weight average molecular weight ($M_w$) was estimated from intrinsic viscosity measurement using the Mark-Howink Sakurada relation (Harding S., Vårum K. M., Stokke B. T. and O. Smidsrod. 1990. Molecular weight determination of polysaccharide. Advances in Carbohydrate Chemistry. Vol 1. JAI press., in press.). Aqueous solutions of sodium chloride (0.1M) were used at 20° C. in a Ubbelohde suspended capillary viscometer with an automatic dilution viscosity system (Scott-Geräte). From this high molecular weight poly-M, samples with different chain length were prepared by partial hydrolysis for 10–120 min. at 100° C. and pH 5.4.

The β1-4 linked glucuronic acid (D-GlcA) (C60XY) prepared by oxidation of cellulose at position C-6 (Painter T. J., Cesaro A., Delben F. and S. Paoletti. 1985. New glucuronoglucan obtained by oxidation of amylose at position 6. Carbohydr. Res., 140:61), was provided by Dr. A. Cesaro, Trieste, Italy. The molecular weight ($M_w$) was estimated by viscometry to be 60,000; and the degree of oxidation (94%) was determined by potentiometric titration.

Chitin was isolated (Hacman R. H. 1954. Studies on chitin. I. Enzymic degradation of chitin and chitin esters. Aust. J. Biol. Sci., 7:168) from shrimp shell and milled in a hammer mill to pass through a 0.5 mm sieve. N-deacetylation of chitin under homogeneous conditions involved the procedure of Sannan et. al. (Sannan T., Kurita K. and Y. Iwakura. 1976. Studies on Chitin. 2. Effect of Deacetylation on Solubility. Macromol. Chem., 177:3589). The degree of deacetylation (40%) was determined by high-field N.M.R.-spectroscopy (Vårum K. M., Anthonsen M. W., Grasdalen H. and O. Smidsrod. 1990. N.m.r. Spectroscopy of partially N-deacetylated Chitins (Chitosans). I. Determination of the Degree of N-acetylation and the Distribution of N-acetyl Groups. Carbohydr. Res., In Press). Chitosan was dissolved in acetic acid (2% w/v) by gentle shaking overnight at ambient temperature. Chitosan of different molecular weight were prepared by adding a known amount (10–100 mg) of solid $NaNO_2$, each solution was stored in the dark at room temperature overnight, and finally neutralized with NaOH. The degraded chitosans were conventionally reduced with sodium-borhydride (250 mg). The pH of the solutions were adjusted to 5 with HCl, the solutions were dialyzed against 0.2M NaCl and distilled water, and finally lyophilized. This converted the chitosans into the chloride salt which is readily soluble in water. The number average molecular weight ($M_n$) was determined by osmotic pressure measurements of solutions of chitosan in a Knauer Membrane Osmometer with a Sartorius SM 11736 cellulose-acetate membrane. Chitosan concentrations of 0.1–0.8% (w/v) were used.

Scleroglucan (SG), a β1-3 linked D-glucose with single β1-6 linked glycopyranose residues on every third monomer with a molecular weight of 384,000 ($M_w$), was provided by Dr. B. T. Stokke, Institute of Physichs, NTH, University of Trondheim, Trondheim, Norway.

*E. coli* derived LPS (Sigma) (strain 026:B6) was used in these experiments.

Endotoxin contamination in the different polysaccharides was measure by the LAL assay (Kabi vitrum, Stockholm, Sweden). The levels of endotoxin were as follows:

1 μg of C60XY contains 40 pg
1 mg of chitosan contains 1.3 pg
1 mg of SG contains 72 pg.

Monocyte Cultivation

Monocytes were isolated from human A+ blood buffy coat (The Bloodbank, University of Trondheim, Norway) as described by Boyum (Boyum AM. 1976. Separation of monocytes and lymphocytes. Scan. J. Immunol., 5:9). Monocytes in 24 well culture plates (Costar, Cambridge, Mass., USA) were cultured in complete medium consisting of RPMI 1640 (Gibco, Paisley, U.K.) with 1% glutamine, 40 μg/ml garamycin and 25% A+ serum (The Bloodbank, University of Trondheim).

The different polysaccharides and LPS were dissolved in PBS and sterile filtered through 0.2 μm filter (Nuclepore, Pleasanton, Calif.). The polysaccharide and LPS solutions were diluted in complete medium and added to the monocytes for 16–24 hours before the supernatants were harvested. Some monocyte cultures were preincubated with recombinant (r) human IFN-γ (rIFN-γ, Genentech, Inc. South San Francisco, Calif.) for 30. min. before the polysaccharides and LPS were added.

Animals

8–11 week old female $CB_6F_1$ mice were purchased from Bomholdt Gård Breeding Research Center, Ry, Denmark. The mice were allowed access to ordinary chow and water ad libitum and weighed 20–22 g on the day of the study.

In Vivo Experiment

For cytokine induction mice were injected iv. with 0.2 ml of sterile saline containing 250 μg of C60XY. At different time points after injection three mice were sacrificed and bled for separation of serum. Individual serum samples were kept in sterile tubes at −20° C. until tested for TNF-α and IL-6 activities.

Assay for Detection of TNF-α in Supernatants from Monocytes

TNF-α activity was determined by its cytotoxic effect on the fibrosarcoma cell line WEHI 164 clone 13, as described (Espevik T. and J. Nissen-Meyer. 1986. A highly sensitive cell line, WEHI 164 clone 13, for measuring cytotoxic factor/tumor necrosis factor from human monocytes. J. Immunol. Methods, 95:99). Dilutions of rTNF-α (rTNF-α (human) and rMuTNF-α, Genentech) were included as a standard. The TNF-α specificity of the assay was verified by using a monoclonal antibody against rTNF-α which completely neutralized the recorded activity (data not shown). Results are presented as ng/ml±S.E. of triplicate determinations.

Assay for Detection of IL-1 in Supernatants from Monocytes

IL-1 activity was determined by a two stage assay. The first stage involves the mouse thymocyte EL4 NOB-1 cell line which produces high concentrations of Interleukin-2 (IL-2) in response to human IL-1, as described by Gaering et al. (Gearing A. J. H., Bird C. R., Bristow A., Poole S. and R. Thorpe. 1987. "A simple sensitive bioassay for Interleukin-1 which is unresponsive to $10^3$ U/ml of Interleukin-2." J. Immunol. Methods, 99:7). Dilutions of rIL-1$\beta$ (Glaxo, Geneva Switzerland) were included as standard. After incubation in 37° C., 5% $CO_2$ atm. for 24 hours 100 $\mu$l of the supernatants were transferred into a replicate 96-well microplate. The second stage in this assay involves the IL-2 dependent mouse T cell line HT-2 as described by Mosmann, T. (Mosmann T. R., Cherwinski H., Bond M. W., Giedlin M. A. and R. L. Coffman. 1986. Two types of murine helper T cell clone. I. Definition according to profiles of lymphokine activities and secreted proteins. J. Immunol., 136:2348). One hundred $\mu$l of HT-2 suspension ($1.5 \times 10^5$ cells/ml) were added to each well and incubated for an additional 24 hours. The IL-1 activity was completely neutralized by two polyclonal antibodies against rIL-1b and rIL-1a (gift from Dr. A. Shaw, Glaxo, Geneva, Switzerland), (data not shown). Results are presented in Table 2 as ng/ml±S.E. of triplicate determinations.

Assay for Detection of IL-6 in Supernatants from Monocytes

IL-6 activity was determined by the IL-6 dependent mouse hybridoma cell line B.13.29 clone 9, as described by Aarden et al. (Aarden L. A., De Groot E. R., Schaap O. L. and P. M. Lansdorp. 1987. Production of hybridoma growth factor by monocytes. Eur. J. Immunol., 17:1411). Dilutions of the supernatants and rIL-6 (Brakenhoff J. P. J., De Groot E. R., Evers R. F., Pannekoekh H. and L. A. Aarden. 1987. Molecular cloning and expression of hybridoma growth factor in Escherichia coli. J. Immunol., 139:4116) as a standard, were incubated in a 96-well microplate together with cells ($5 \times 10^4$ cells/ml) for 72 hours. The plates were harvested and the IL-6 activity was determined colorimetrically (see below). The IL-6 activity was completely neutralized by a polyclonal antibody against rIL-6 (gift from Dr. W. Fiers, University of Ghent, Belgium), (data not shown). Results are presented in Table 2 as ng/ml±S.E. of triplicate determinations.

MTT-assay (3-(4,5-dimethylthiazol-2-yl)-2,5-diphenyl tetrazolium bromide)

Viability in the assays for TNF-$\alpha$, IL-1 and IL-6 were measured in a colorimetric assay for growth and survival by using a tetrazolium salt as described by Mosmann (Mosmann T. 1983. Rapid colorimetric assay for cellular growth and survival: Application to proliferation and cytotoxicity assays. J. Immunol. Methods, 65:55).

Results

Figure 1:
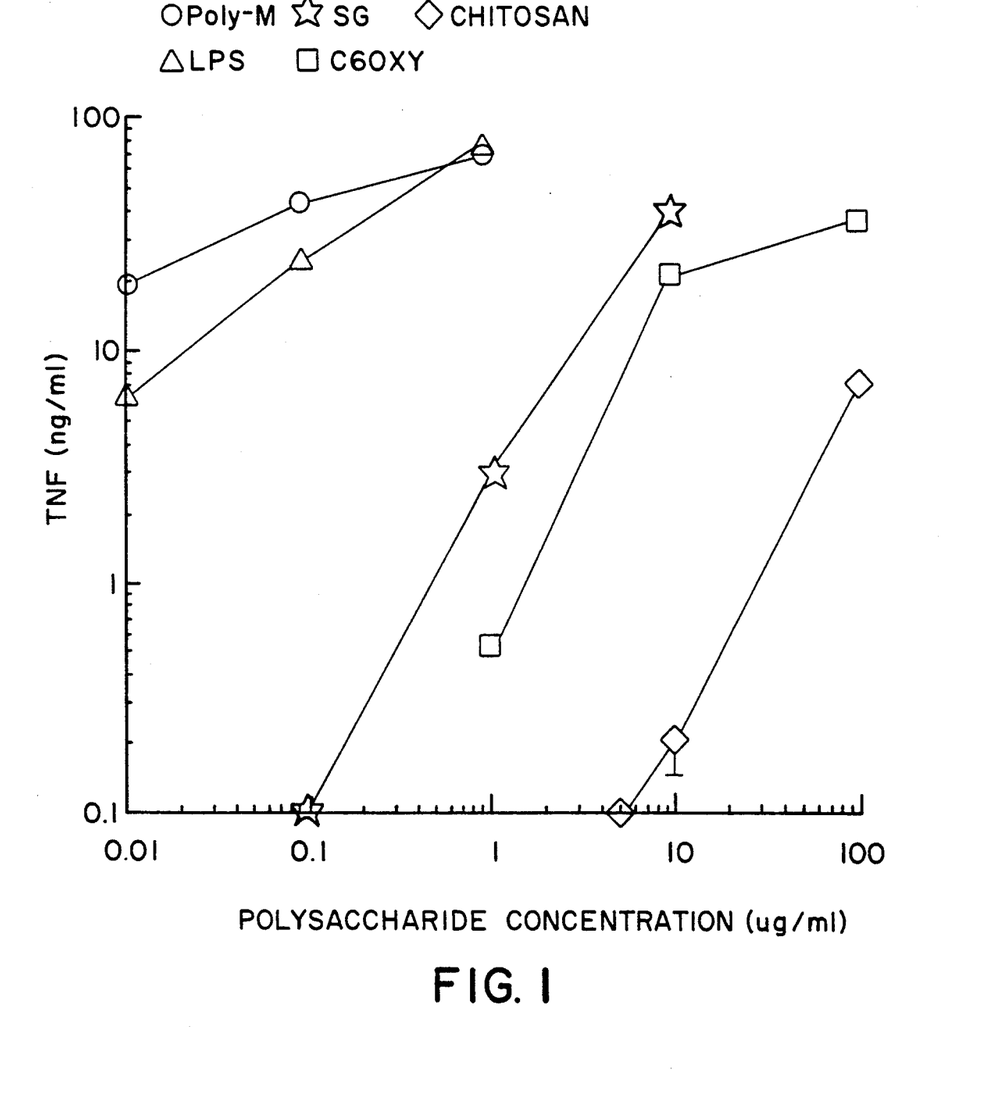
FIG. 1 is a graph showing the production of TNF-α from monocytes stimulated with poly-M (circle), LPS (triangle), SG (star), C6OXY (square) and chitosan (diamond). Production of TNF-α from unstimulated monocytes was less than 0.1 ng/ml.

We have previously shown that blocks of $\beta$1-4 linked D-ManA (M-blocks) isolated from the algea *Ascophyllum nodosum* stimulated human monocytes to produce TNF-$\alpha$, IL-1 and IL-6 (Otterlei M., Ostgaard K., Skjåk-Br k G., Smidsrod O. and T. Espevik. 1990. Induction of cytokine production from human monocytes stimulated with alginate. J. of Immunotherapy, 1991, In press). In the present invention we have isolated polymers of $\beta$1-4 linked D-ManA (poly-M) from *Pseudomonas aeruginosa* and compared its TNF-$\alpha$ inducing ability with other $\beta$1-4 and $\beta$1-3 linked polysaccharides. FIG. 1 shows that poly-M is approximately equally potent as LPS, around 100 times more potent than $\beta$1-3 linked D-glucose (SG), 500 times more potent than cellulose oxidized in C-6 position (C60XY) and 10,000 times more potent than chitosan in their respective abilities to induce production of the cytokines.

Since the poly-M was isolated and purified from liquid cultures of a Gram negative bacteria, the possibility existed that the high TNF-$\alpha$ stimulating activity could be due to LPS contamination. However, LPS levels in the poly-M preparation was less than 1 ng in 1 $\mu$g of poly-M. Since *E. coli* LPS at 1 ng/ml did not stimulate TNF-$\alpha$ production from monocytes (data not shown) it was shown that LPS contamination was not the cause of the stimulating activity. Furthermore, reduction of the LPS content in the poly-M preparation by using a polymyxin B column and a dialyzable surfactant, octyl-$\beta$-D-glycopyranoside (Karplus T. E., Ulevitch R. J. and C. B. Wilson. 1987. A new method for reduction of endotoxin contamination from protein solutions. J. Immunol. Methods, 105:211) did not reduce its TNF-$\alpha$ stimulating ability (data not shown). Consequently, it is unlikely that the stimulatory effect of poly-M at 0.1 $\mu$g/ml and 0.01 $\mu$g/ml is due to LPS contamination.

Figure 2:
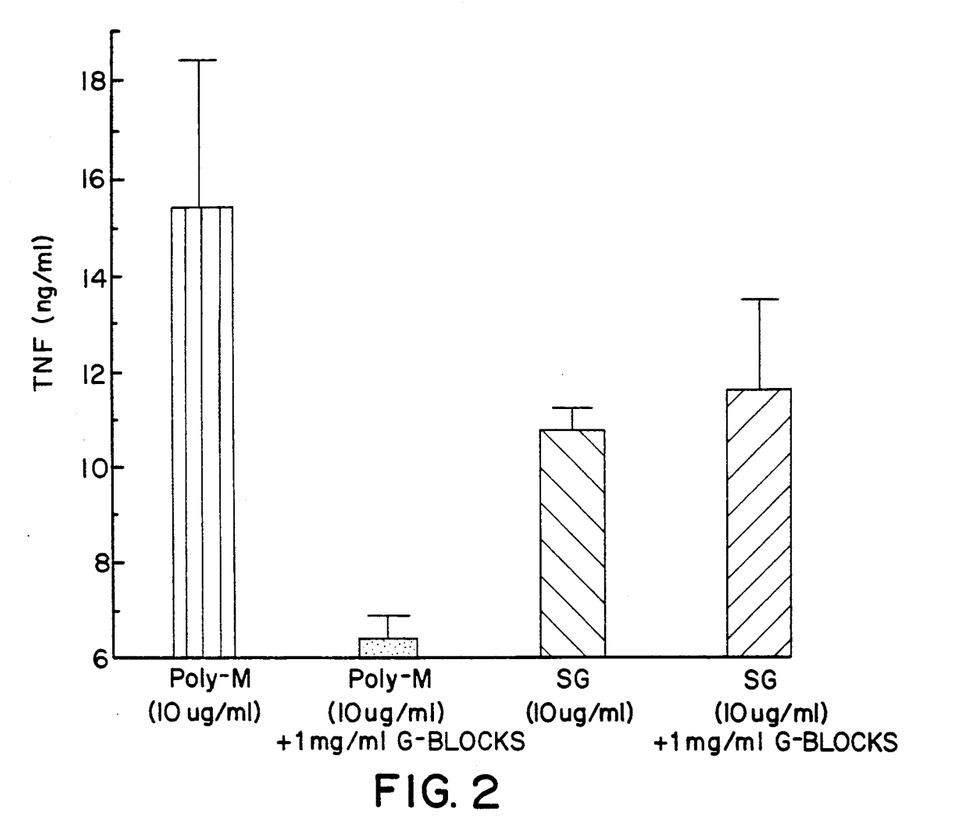
FIG. 2 is a graph showing the production of TNF-α from monocytes stimulated with samples of poly-M (a) and chitosan (b) with different molecular weights. Production of TNF-α from unstimulated monocytes was less than 0.08 ng/ml.

The prior art established that in order for the $\beta$1-3 glucans to have optimal antitumor activity the molecular weight must be higher than 50,000 (Kojima T., Tabata K., Itoh W. and T. Yanaki. 1986. Molecular Weight Dependence of the Antitumor Activity of Scizophyllan. Agric. Biol. Chem., 50(1):231). It was therefore of interest to examine the relationship between the molecular weight of $\beta$1-4 linked polysaccharides and their TNF-$\alpha$ inducing capability. The results shown in FIG. 2 a and b demonstrate that the molecular weight must be higher than 20,000 and 50,000 for chitosan and poly-M, respectively, in order to obtain maximal stimulatory effect.

Activation of monocytes with IFN-$\gamma$ increases their ability to produce TNF-$\alpha$ in response to LPS (Nissen-Meyer J., Hofsli E., Espevik T. and R. Austgulen. 1988. Involvement of Tumor Necrosis Factor in cytotoxicity Mediated by Human Monocytes. Nat. Immun. Cell Growth Regul., 7:266). We therefore examined whether IFN-$\gamma$ could increase the TNF-$\alpha$ production from polysaccharide stimulated monocytes. Table 2 shows that IFN-$\gamma$ increased the TNF-$\alpha$ production from chitosan, C60XY, SG and poly-M stimulated monocytes in a similar way as for LPS. Therefore, the present invention includes the use of IFN-$\gamma$ in conjunction with the polysaccharides of the present invention in order to increase the stimulation of the cytokine production.

Figure 3:
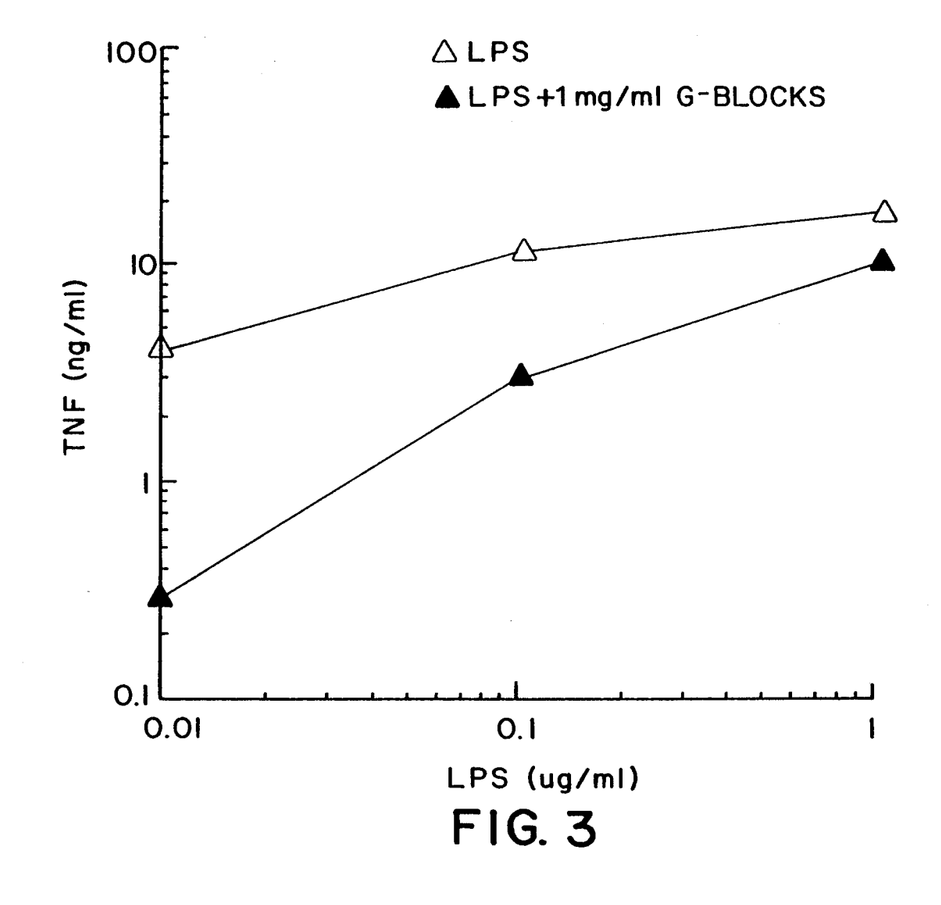
FIG. 3 is a graph over time showing the effect of an injection of 250 mg C6OXY into mice on the production of both TNF-α and IL-6. Background levels were less than 0.003 ng/ml of serum TNF-α and less than 0.019 ng/ml serum IL-6.
Figure 4A:
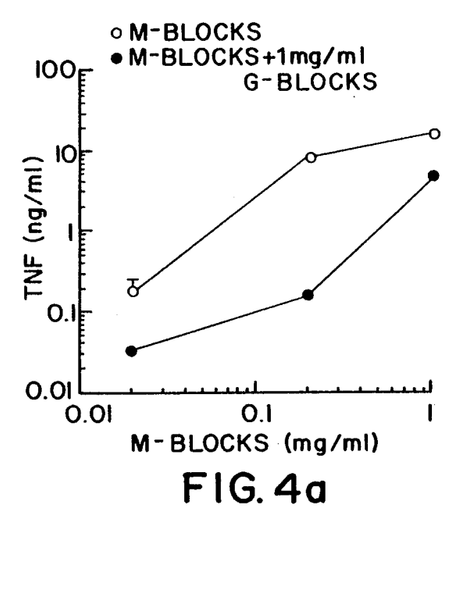
FIG. 4(a), 4(b), 4(c) are a graph showing the inhibition of TNF-α (a), IL-6 (b) and IL-1 (c) production from monocytes stimulated with M-blocks without (open square) and with addition of 1 mg/ml G-blocks (filled square). Production of cytokines from unstimulated monocytes and monocytes stimulated with 1 mg/ml G-blocks were less than 0.01 ng/ml.
Figure 4B:
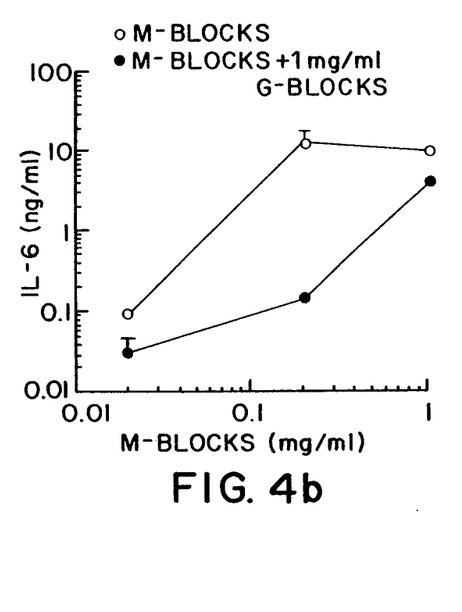
Figure 4C:
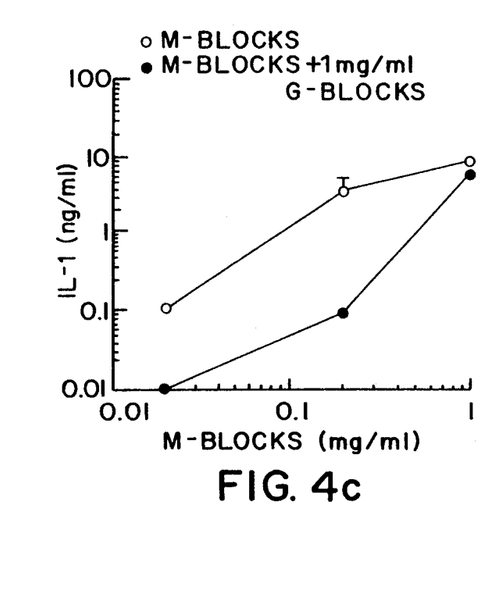

Since polysaccharides consisting of $\beta$1-4 linked poly uronic acids were very potent in stimulating TNF-$\alpha$ production in vitro, we tested whether C60XY had immunostimulating activities in mice. As illustrated in FIG. 3, the injection of 250 $\mu$g C60XY into mice led to the rapid production of both TNF-$\alpha$ and IL-6. Although measurable levels of IL-6, but not TNF-$\alpha$, could be detected 30 min. after injection, the peak level for both cytokines was attained 60 min. after C60XY administration. The activities of both TNF-$\alpha$ and IL-6 were eliminated rapidly reaching baseline levels within 60 minutes of peak time.

In summary, the compositions employed in the present invention are capable of stimulating the effects of leukocyte derived cytokines, such as TNF, IL-1 and IL-6, on phagocytes, such as polymorphonuclear leukocytes.

Because IL-1, IL-6, TNF, and other leukocyte derived cytokines have been implicated in such a wide variety of mammalian conditions, this invention has a similarly broad scope of application. Among the conditions that can be treated or alleviated by the inhibition or stimulation of IL-1, IL-6, TNF, and other leukocyte derived cytokines are: sepsis, septic shock, endotoxic shock, gram negative sepsis, toxic shock syndrome, adult respiratory distress, fever and myalgias due to infection (i.e. influenza), cachexia secondary to infection or malignancy, cachexia secondary to AIDS, rheumatoid arthritis, gouty arthritis, osteoporosis, keloid formation, scar tissue formation, decreased appetite, Crohn's disease, ulcerative colitis, fever due to central nervous system bleeding, glomerulonephritis, multiple sclerosis, Creutzfeld-Jacob disease, adverse reactions to dialysis and psoriasis.

By reference to the specific cause of the disease condition, the more generic term "trauma" can be used. The term "trauma" refers broadly to cellular attack by foreign bodies and physical injury of cells. Included among foreign bodies are microorganisms, particulate matter, chemical agents, and the like. Included among physical injuries are mechanical injuries, such as abrasions, lacerations, contusions, wounds, and the like; thermal injuries, such as those resulting from excessive heat or cold; electrical injuries, such as those caused by contact with sources of electrical potential; and radiation damage caused, for example, by prolonged, extensive exposure to infrared, ultraviolet or ionizing radiations.

Microorganisms included among the foreign bodies that can elicit a biological response are bacilli, fungi and yeast, viruses, parasites, and the like. Representative bacilli are: Actinomyces spp.; Bacteroides spp.; Corynebacterium spp.; Enterobacteriacea; Enterococcus; Haemophilus spp.; Micrococcus spp.; Neissera spp.; *Staphylococcus aureus; Streptococcus pneumoniae; E. coli*; Clostridium spp.; *Streptococrus agalactiae*; Bacillus spp.; *H. influenzae*; Moraxella spp.; Myccbacteria spp.; *Pseudodomonas aeruginosa*; Vibrio spp.; and Mycoplasma.

Representative fungi and yeast that are capable of eliciting a biological response are: Microspurum; Blastomyces; Histoplasma; Aspergillus; Cryptococcus; Candida spp.; Coccidioides; and *Candida albicans*.

Representative viruses are: Rhinovirus; Parainfluenza; Enterovirus; Influenza; Smallpox and vaccinia; Herpes simplex; Measles; Rubella; Arbovirus (Western, Eastern and Venezuelan equine encephalitis, and California encephalitis); Rabies; Colorado tick fever; Yellow fever; Dengue; Hepatitis Virus B (HB Ag); Hepatitis Virus A (HAV); and Human Immunodeficiency Virus (HIV).

Representative parasites that can elicit a response are: *Trypanosoma cruzi; Entamoeba histolytica; Leishmania brasiliensis; Leishmania tropica; Leishmania donovani; Toxiplasma gondii; Plasmodium falcipaum; Trypanosoma rhodesiense; Loa loa; Trichomonas hominis; Schistosoma japonicum; Schistosoma mansoni*; and *Fasciola hepatica*.

Figure 5:
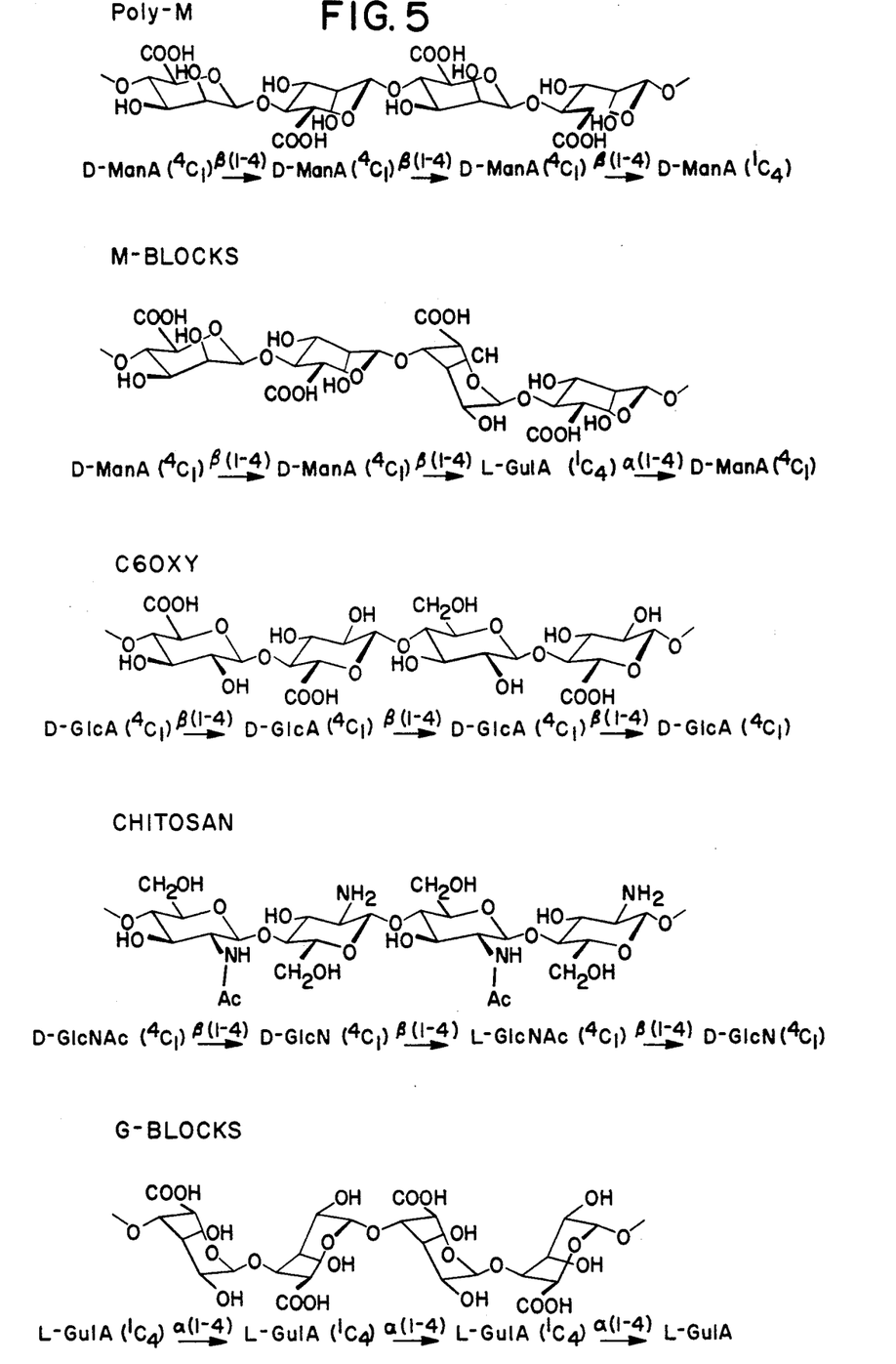
FIG. 5 is a schematic representation of a part of the structures of the different polysaccharides used in this invention.

Thus, it has been demonstrated that polymers of mannuronic acid are a very potent stimulator of TNF-$\alpha$ production from human monocytes. The high TNF-$\alpha$ inducing ability of poly-M was not restricted to poly-M produced by *Pseudomonas aeruginosa*, as similar potency was found for poly-M isolated from liquid cultures of *Pseudomonas syrinqae pv phaseolicola* (Gross M. and K. Rudolph. 1983. Studies on the extracellular polysaccharides (EPS) produced in vitro by *Pseudomonas phaseolicola*. J. Phytopathology, 118:276 (unpublished data)). Poly-M is 100 times more potent than SG, 500 times more potent than C6OXY and 10,000 more potent than chitosan. It has previously been reported that the anti-tumor effects of $\beta$1-3 glucans are optimal at a molecular weight of over 50,000 (Kojima T., Tabata K., Itoh W. and T. Yanaki. 1986. Molecular Weight Dependence of the Antitumor Activity of Scizophyllan. Agric. Biol. Chem., 50(1):231) and that the anti-tumor effect is mediated by cytokines (Seljelid R., Figenschau Y., Bogwald J., Rasmussen L. T. and R. Austgulen. 1989. Evidence that Tumour Necrosis Induced by Aminated $\beta$1-3D Polyglucose is Mediated by a Concerted Action of Local and Systemic Cytokines. Scand. J. Immunol., 30:687). Our data indicate that maximal production of TNF-$\alpha$ occurred when the molecular weight of poly-M and chitosan was above 50,000 and 20,000 respectively. The difference in the potency to induce TNF-$\alpha$ production may be related to the polysaccharide structure as the molecular weight of the polysaccharides used was higher than 50,000 (Table 1). From FIG. 5 it can be seen that Poly-M is a homopolymer composed of $\beta$1-4 linked D-ManA while chitosan is composed of randomly distributed units of $\beta$1-4 linked N-acetylglucosamine (D-GlcNAc) and N-glucosamine (D-GlcN) (Várum K.M., Anthonsen M. W., Grasdalen H. and O. Smidsrod. 1990. N.m.r. Spectroscopy of Partially N-deacetylated Chitins (Chitosans). I. Determination of the Degree of N-acetylation and the Distribution of N-acetyl Groups. Carbohydr. Res., In Press). The three dimensional (3D) structure of C6OXY and poly-M is similar, but the sequences of $\beta$1-4 linked D-guluronic acid (D-GlcA) in C6OXY are broken by $\beta$1-4 linked D-glucose (D-Glc) (6%). The homopolymeric sequences of $\beta$1-4 linked uronic acids will consequently be shorter in C6OXY than in poly-M. One possibility is that the high TNF-$\alpha$ inducing ability of poly-M compared to C6OXY is caused by the longer homopolymeric $\beta$1-4 linked uronic acid blocks. Additional structural similarities between the TNF-$\alpha$ stimulating polysaccharides poly-M, chitosan and C6OXY are equal in length between the monomers along the chains due to di-equatorial (di-eq) glycosidical bindings between the monomers (FIG. 5). These similarities in 3D structure are probably important for the TNF-$\alpha$ stimulating activity of poly-M, chitosan and C6OXY.

The bacteria *Pseudomonas aeruqinosa* is found in most patients with cystic fibrosis and colonization is associated with pulmonary damage (Simpson J. A., Smith S. E. and Dean R. T. 1988. Alginate Inhibition of Uptake of *Pseudomonas aeruqinosa* by Macrophages. J. Gen. Microbiol., 134:29). The facts that high molecular (viscous) poly-M is produced by *Pseudomonas aeruginosa*, that poly-M is a very potent cytokine stimulator and that no enzyme in the human body is known to degrade poly-M could explain some of the difficulties in treating this infection in man.

Injection of 250 $\mu$g C6OXY in mice resulted in the release of TNF-$\alpha$ and IL-6 into the circulation. The serum concentrations of TNF-$\alpha$ and IL-6 from mice injected with C6OXY are not due to LPS contamination as I $\mu$g C6OXY contained only 40 pg endotoxin, and injection of 10 ng LPS resulted in less than 27 pg/ml TNF-$\alpha$ and less than 21.5 ng/ml IL-6 in serum. In addition Shalaby et. al. (Shalaby R. M., Waage A., Aarden L. and T. Espevik. 1989. Endotoxin, Tumor Necrosis Factor-$\alpha$ and Interleukin 1 Induce Interleukin 6 Production in vivo. Clinic. Immunol. and Immunolpath. 53 488) have shown that the kinetics for serum TNF-α are different from the kinetics for serum IL-6 after LPS injection into mice. They found that peak serum IL-6 concentration was attained after 2 hr of LPS injection into mice, while the peak for TNF-α is attained after 1 hr. In this experiment the peak level for both cytokines was attained 1 hr after C6OXY administration. These data indicate that di-eq β1-4 linked poly uronic acids have potent immune stimulating activities in vivo.

Previously we have found that G-blocks are ineffective in stimulating monocytes to produce cytokines. Otterlei M., Ostgaard K., Skjåk-Br k G., Smidsrod O. and T. Espevik. 1991. Induction of cytokine production from human monocytes stimulated with alginate, J. of Immunotherapy, in press. Poly-M and C6OXY have similar polysaccharide structure. Furthermore, as discussed above, the only structural difference between poly-M and M-blocks is the length of the homopolymeric D-ManA sequence (FIG. 5). In the M-blocks this sequence is broken up by L-GulA residues (5%) giving an average number of 5-7 consecutive D-ManA residues. The glycosidic linkages in M-blocks are di-eq with a monomer length 5.17 Å in the fully stretched form (Atkins E. D. T., Mackie E. E. and F. E. Smolko. 1970. Crystalline structure of alginic acid. Nature 225:626), but when a D-ManA is linked to a L-GulA instead of D-ManA the glycosidic linkage is a equatorial-axial (eq-ax) nature (FIG. 5). The length between the monomers in a eq-ax binding is shorter than in a di-eq binding. Since D-ManA and L-GulA have almost identical structures (different only in the configuration around C-5) the large difference between M- and G-blocks ability to stimulate cytokine production must be due to the difference in the conformation they adapt as part of a homopolymeric structure (see FIG. 5).

The G-blocks have mainly di-axially (di-ax) glycosidic linkages which are even shorter (4.36 Å) than the eq-ax binding (Atkins E. D. T., Mackie E. E. and F. E. Smolko. 1970. Crystalline structure of alginic acid. Nature 225:626). G-blocks will also contain some ax-eq linkages between L-GulA and D-ManA (10%). The G-blocks are more compact than M-blocks, C6OXY and poly-M but the chains have all two folded screw axis in the solid state and statistical mechanical calculations has shown that this linkage conformation is also highly populated in solutions (Smidsrod O., Haug A. and S. Whittington. 1972. The molecular basis for some physical properties of polyuronides. Acta. Chem. Scand. 26:2563; Smidsrod O., Glover R. M. and S. G. Whittington. 1973. The relative extension of alginates having different chemical compositions. Carbohydr. Res. 27:107).

TABLE 2

Effects of IFN-γ on polysaccharide induced TNF-α [ng/ml] production from human monocytes.

| Addition | Concentrations (μg/ml) | TNF-α [ng/ml] −IFN-γ | TNF-α [ng/ml] +IFN-γ (1000 U/ml) |
|---|---|---|---|
| Medium | — | <0.1 | <0.1 |
| Chitosan | 100 | 7.0 ± 0.4 | 32.7 ± 7.8 |
| C6OXY | 100 | 34.2 ± 3.6 | 68.9 ± 11.1 |
| SCLE-1 | 1 | 2.9 ± 0.5 | 10.3 ± 2.3 |
| Poly-M | 0.1 | 45.8 ± 1.7 | 93.5 ± 19.7 |
| LPS | 0.1 | 23.7 ± 3.9 | 47.8 ± 10.1 |

We claim:

1. A method of stimulating cytokine production comprising the step of providing monocytes in vivo or in vitro with an effective amount of a material selected from the group consisting of diequatorial bound β1-4 polyuronic acid and chitosans, whereby cytokine production by said monocytes is induced or increased.

2. The method of claim 1 wherein said diequatorial bound β1-4 polyuronic compounds are selected from the group consisting of polymers of different size of β1-4 linked D-mannuronic acid and cellulose oxidized in C-6 position (C6OXY).

3. The method of claim 1 wherein said diequatorial bound β1-4 polyuronic compound is β1-4 linked D-ManA.

4. The method of claim 3 wherein said β1-4 linked D-ManA has a molecular weight greater than 50,000.

5. The method of claim 1 wherein said chitosan has a molecular weight greater than 20,000.

6. The method of claim 1 further comprising the step of providing said monocytes with an effective amount of IFN-γ prior to providing said diequatorial bound β1-4 polyuronic acid.

7. A method of stimulating monocyte production of IL-1, IL-6 and TNF-α in vivo or in vitro comprising the step of providing said monocytes with an effective amount of a material selected from (1) diequatorial bound β1-4 polyuronic compounds selected from the group consisting of (a) polymers of β1-4 linked D-mannuronic acid and (b) cellulose oxidized in C-6 position (C6OXY), and (2) chitosans, whereby cytokine production by said monocytes is induced or increased.

8. The method of claim 7 wherein said β1-4 linked D-ManA has a molecular weight greater than 50,000.

9. The method of claim 7 wherein said chitosan has a molecular weight greater than 20,000.

10. The method of claim 7 further comprising the step of providing said monocytes with an effective amount of IFN-γ prior to treatment with said diequatorial bound β1-4 polyuronic acid or chitosans.

11. The method of claim 7 wherein said method is conducted in vivo wherein said providing step consists

TABLE 1

| POLYSACCHARIDE | LINKAGE | MW/DP$_n$ | MONOMER COMPOSITION |
|---|---|---|---|
| Poly-M | β1-4 | [1]270,000 (M$_w$) | 100% D-mannuronic acid |
| M-blocks | β1-4 | DP$_n$ = 30-35 | 95% D-mannuronic acid, 5% L-guluronic acid |
| C6OXY | β1-4 | 60,000 (M$_w$) | 94% D-glucuronic acid, 6% D-glucose |
| Chitosan | β1-4 | [1]100,000 (M$_n$) | 60% N-acetylglucosamine 40% N-glucosamine |
| G-blocks | α1-4 | DP$_n$ = 25-30 | 90% L-guluronic acid 10% D-mannuronic acid |
| SG | β1-3 | 384,000 (M$_w$) | 100% D-glucose |

[1]Samples used in FIG. 1 of injecting into a host an effective amount of said composition.

12. A method of treating a bacterial or fungal infection comprising the step of providing to a host an effective amount of a composition selected from the group consisting of diequatorial bound β1-4 polyuronic acid and chitosans.

13. A method of treating a viral infection comprising the step of providing to a host an effective amount of a composition selected from the group consisting of diequatorial bound β1-4 polyuronic acid and chitosans.

14. A method of treating neoplasia comprising the step of providing to a host an effective amount of a composition selected from the group consisting of diequatorial bound β1-4 polyuronic acid and chitosans.

15. A composition for stimulating cytokine production comprising β1-4 linked D-ManA having a molecular weight greater than 50,000 and a pharmaceutically acceptable carrier.

16. The composition of claim 15 further comprising an effective amount of IFN-γ.

* * * * *

UNITED STATES PATENT AND TRADEMARK OFFICE
CERTIFICATE OF CORRECTION

PATENT NO. : 5,169,840

DATED : December 8, 1992

INVENTOR(S) : Otterlei et al.

It is certified that error appears in the above-identified patent and that said Letters Patent is hereby corrected as shown below:

On the title page,

At line 4 of the Abstract, in the second sentence change

"⊕ 1-4" to -- β 1-4 --

Signed and Sealed this

Fourth Day of April, 1995

Attest:

BRUCE LEHMAN

*Attesting Officer*  *Commissioner of Patents and Trademarks*